(12) United States Patent
Brookmire (10) Patent No.: US 8,585,984 B2
(45) Date of Patent: Nov. 19, 2013

(54) PROBOSCIS FOR USE WITH A DIAGNOSTIC INSTRUMENT

(75) Inventor: Michael Andrew Brookmire, Falmouth, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 22 days.

(21) Appl. No.: 13/295,614

(22) Filed: Nov. 14, 2011

(65) Prior Publication Data

US 2012/0121479 A1 May 17, 2012

Related U.S. Application Data

(60) Provisional application No. 61/456,954, filed on Nov. 15, 2010.

(51) Int. Cl.
*B01L 3/02* (2006.01)
*B01L 3/00* (2006.01)

(52) U.S. Cl.
USPC ........ 422/501; 422/520; 422/521; 73/863.32; 73/864; 73/864.01

(58) Field of Classification Search
USPC ................ 422/501, 509, 518, 544, 520, 521; 73/864.32, 864, 864.01
See application file for complete search history.

(56) References Cited

U.S. PATENT DOCUMENTS

| | | | | |
|---|---|---|---|---|
| 4,038,650 A | * | 7/1977 | Evans et al. | 340/619 |
| 4,267,150 A | * | 5/1981 | Firestone | 422/545 |
| 5,440,940 A | * | 8/1995 | Wilkins | 73/864.16 |
| 5,460,782 A | * | 10/1995 | Coleman et al. | 422/520 |
| 5,945,070 A | * | 8/1999 | Kath et al. | 422/535 |
| 6,706,245 B2 | * | 3/2004 | Neal et al. | 422/501 |
| 7,182,915 B2 | * | 2/2007 | Bullen et al. | 422/501 |
| 7,963,159 B2 | * | 6/2011 | Ingram et al. | 73/146.3 |
| 8,460,617 B2 | * | 6/2013 | Schacher et al. | 422/525 |
| 2002/0076826 A1 | * | 6/2002 | Jacobs et al. | 436/174 |
| 2011/0058961 A1 | * | 3/2011 | Sabini et al. | 417/63 |
| 2013/0020232 A1 | * | 1/2013 | Turner et al. | 422/129 |
| 2013/0020236 A1 | * | 1/2013 | Turner et al. | 422/129 |

* cited by examiner

*Primary Examiner* — Brian R Gordon
(74) *Attorney, Agent, or Firm* — Gerald T. Bodner (57) ABSTRACT

A proboscis for use with a diagnostic instrument includes an elongated main body having a proximal end and an opposite distal end, and a lumen extending between the proximal and distal ends. The distal end includes an orifice which is in fluid communication with the lumen. A fluid splash guard is affixed to the main body at the distal end, and provides protection for the orifice and lumen from being clogged with a sample fluid.

16 Claims, 6 Drawing Sheets

FIG. 12

PROBOSCIS FOR USE WITH A DIAGNOSTIC INSTRUMENT

CROSS-REFERENCE TO RELATED APPLICATIONS

This application is related to U.S. Provisional Application Ser. No. 61/456,954, which was filed on Nov. 15, 2010, and is entitled "Proboscis For Use With A Diagnostic Instrument", the disclosure of which is hereby incorporated by reference and on which priority is hereby claimed.

BACKGROUND OF THE INVENTION

1. Field of the Invention

The present invention generally relates to diagnostic instruments such as hematology analyzers, blood chemistry analyzers and other instruments that determine certain physiological properties of patients, and more specifically relates to blood and serum sample metering devices used in such diagnostic instruments. Even more particularly, the present invention relates to a proboscis used in the sample metering devices of such diagnostic instruments.

2. Description of the Prior Art

Many diagnostic instruments, such as hematology analyzers and wet and dry blood chemistry analyzers, employ a sample metering device which is engineered to aspirate and dispense precise minute volumes of a fluid. The metering device often includes a metering probe, or proboscis, on which is removably fitted a disposable plastic tip.

Figure 1:
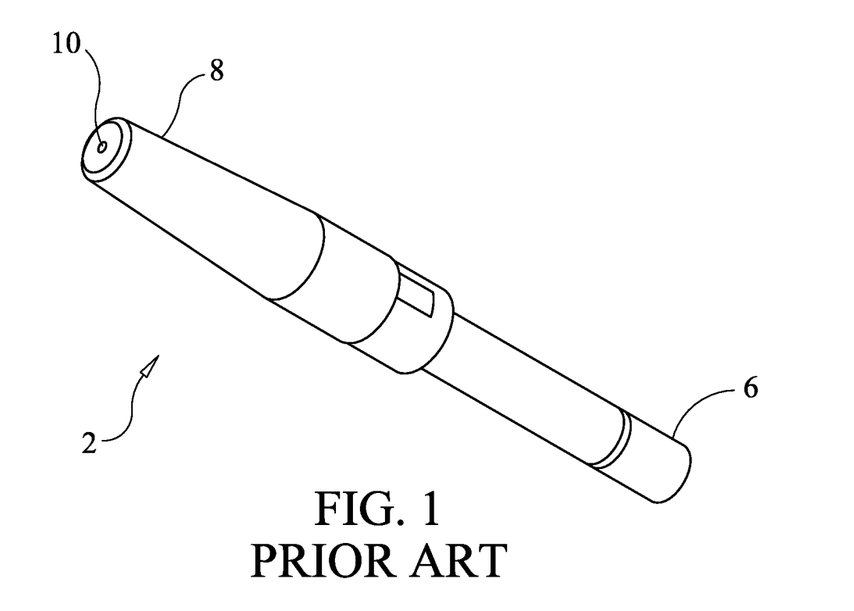
FIG. 1 is a perspective view of a conventional proboscis used with a diagnostic instrument.
Figure 2:
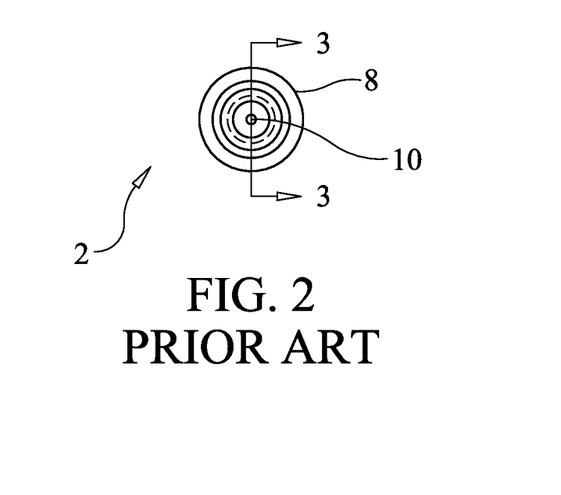
FIG. 2 is an elevational view of the distal end of the conventional proboscis shown in FIG. 1.
Figure 3:
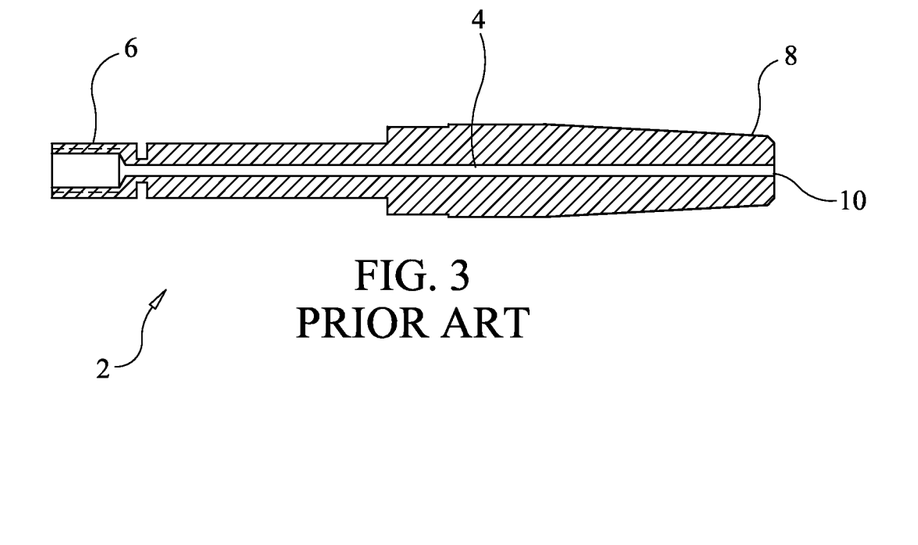
FIG. 3 is a longitudinal cross-sectional view of the conventional proboscis shown in FIGS. 1 and 2, taken along line 3-3 of FIG. 2.
Figure 4:
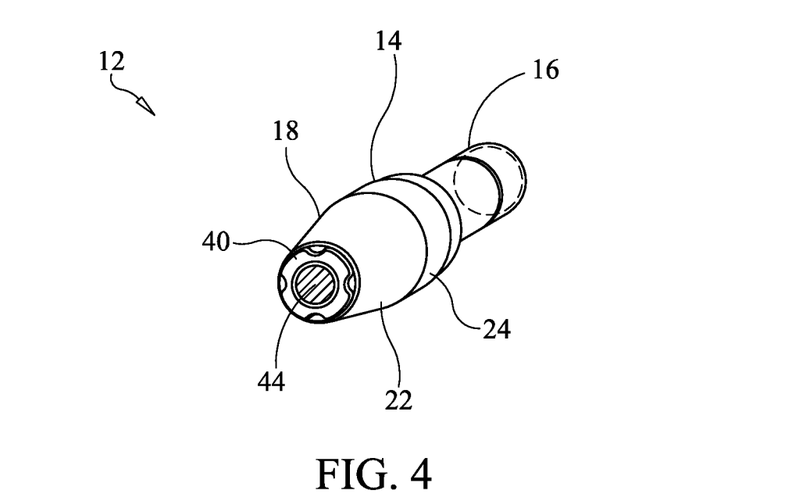
FIG. 4 is a front perspective view of an improved proboscis formed in accordance with the present invention.
Figure 5:
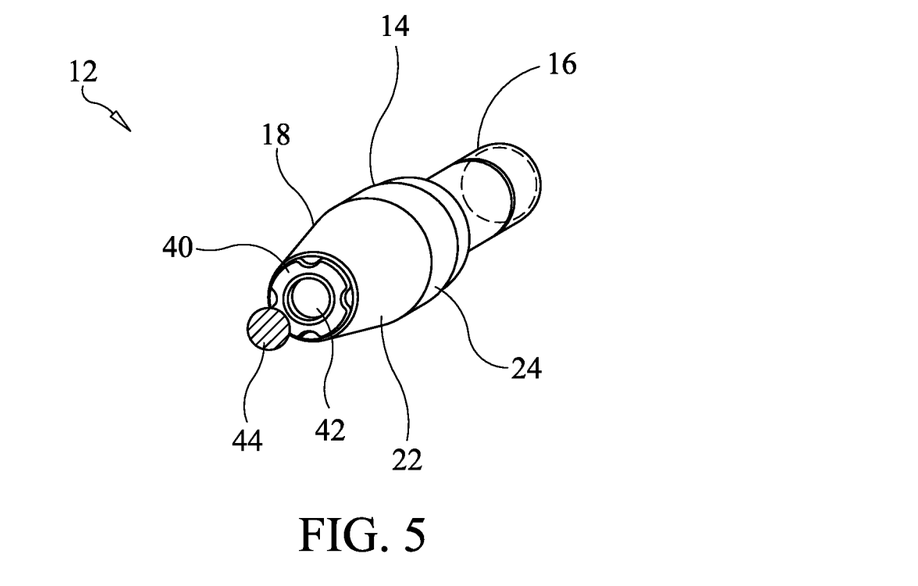
FIG. 5 is a front perspective, partially exploded view of the improved proboscis of the present invention shown in FIG. 4.
Figure 6:
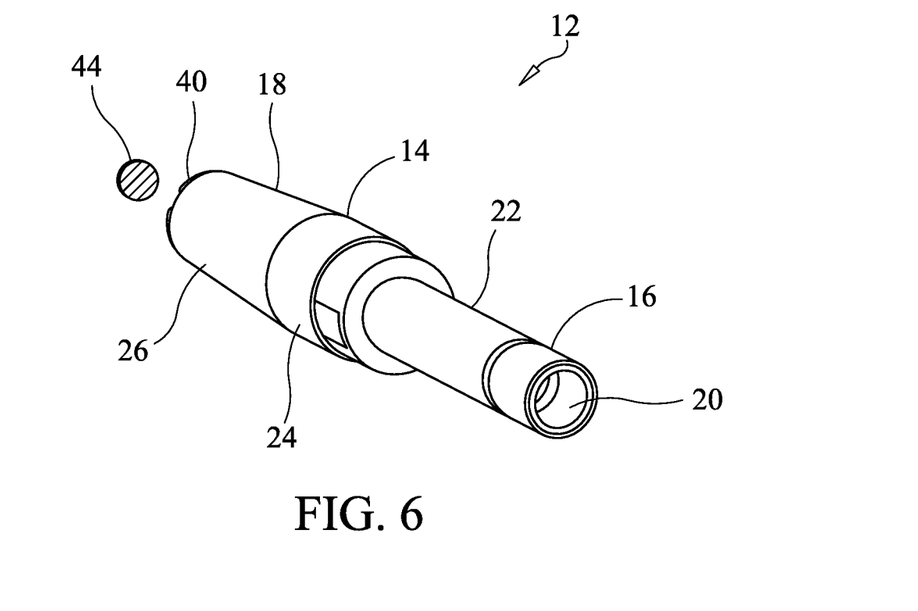
FIG. 6 is a rear perspective, partially exploded view of the improved proboscis of the present invention shown in FIGS. 4 and 5.

FIGS. 1-3 illustrate one form of a conventional proboscis 2 used in a dry chemistry analyzer. The proboscis 2 has formed therein a lumen 4 of constant diameter extending axially therethrough from its proximal end 6, where it is coupled to a metering pump forming part of the overall sample metering device of the diagnostic equipment, to its distal free end 8, which has a relatively small orifice 10 through which the lumen 4 is in fluid communication with the disposable tip situated on the distal end 8 of the proboscis 2. The metering pump creates a partial vacuum or partial pressure within the proboscis lumen 4, and concomitantly within the disposable tip, to selectively draw into the tip or dispense therefrom a specific amount of a sample liquid, such as blood, serum, a chemical reagent or the like. The disposable plastic tip mounted on the distal end portion 8 of the proboscis 2 is removed therefrom and properly discarded after the sample metering operation has been completed.

The diagnostic instrument handles sample fluids (blood, serum, chemical reagents or the like) which by their very nature can be sticky substances that can, over time, coagulate or adhere to surfaces they contact. The blood sample, serum, chemical reagent or other sticky substance may splash onto the distal end 8 of the proboscis 2 when the sample liquid is being aspirated, or perhaps when there is a bubble in the aspirated or expelled sample fluid which bursts, or if the proboscis 2 is not moved smoothly by the sample metering device in either an axial direction or a lateral direction. The fluid held by the disposable tip may enter the lumen 4 or coat the lumen orifice 10 and clog or constrict the orifice or lumen, thereby possibly affecting the accuracy of any metering operation performed by the diagnostic instrument or rendering the instrument inoperable.

OBJECTS AND SUMMARY OF THE INVENTION

It is an object of the present invention to provide a proboscis for use with a diagnostic instrument which minimizes the possibility of the proboscis becoming clogged or inoperative during use.

It is another object of the present invention to provide a proboscis for use with a diagnostic instrument which is engineered with a splash guard.

It is still another object of the present invention to provide a proboscis for use with a diagnostic instrument which is structured to define a tortuous path through the proboscis for aspirated or expelled air to follow.

It is yet another object of the present invention to provide a proboscis with an enlarged lumen which is less likely to clog or become constricted.

It is a further object of the present invention to provide a proboscis for use with a diagnostic instrument which overcomes the inherent disadvantages of conventional proboscises used on diagnostic instruments.

In accordance with one form of the present invention, an improved proboscis for use with a diagnostic instrument includes an elongated main body. The main body has a first end portion (the proximal end) and a second end portion (the distal end) disposed axially opposite the first end portion. The first end portion is typically coupled to a tube which, in turn, is coupled to a metering pump. The second end portion of the proboscis is configured and dimensioned to be removably fitted with a disposable plastic tip.

The main body of the proboscis has a lumen extending axially therethrough between the first end portion (the proximal end) and the second end portion (the distal end). The second end portion has at least one orifice formed therein which is in fluid communication with the lumen of the proboscis.

The improved proboscis further includes a fluid splash guard. The splash guard is affixed to the main body of the proboscis at the second end portion thereof. The splash guard is situated in proximity to the at least one orifice and is more distally located than the at least one orifice on the main body of the proboscis. The splash guard is provided to minimize any contact of fluid (serum, blood sample, chemical reagent or the like) with the at least one orifice which may be caused by splashing of the fluid within the disposable tip.

These and other objects, features and advantages of the present invention will be apparent from the following detailed description of illustrative embodiments thereof, which is to be read in connection with the accompanying drawings.

DETAILED DESCRIPTION OF THE PREFERRED EMBODIMENTS

FIGS. 4-12 illustrate the structure of an improved proboscis 12 for use with a diagnostic instrument, such as a hematology analyzer or a blood chemistry analyzer, constructed in accordance with the present invention. The improved proboscis 12 includes an elongated main body 14, preferably formed from stainless steel or other non-corroding material when placed in contact with air or a liquid, such as water, serum, blood, chemical reagents and the like. The main body 14 of the proboscis 12 is preferably cylindrical in overall shape, and includes a first end portion 16, also referred to herein as a proximal end portion, and a second end portion 18, also referred to herein as a distal end portion, disposed axially opposite the first end portion 16. The proximal end portion 16 includes an end bore 20 which is internally threaded so that it may fluid tightly receive the threaded end of a flexible tube (not shown). The other end of the flexible tube is coupled to a metering pump (also not shown), which forms part of a fluid metering device of a diagnostic instrument.

The distal end portion 18 of the main body 14 of the proboscis 12 receives a disposable plastic tip which, after a metering operation of the diagnostic instrument has been performed, is removed from the proboscis and properly discarded. The disposable tip has an overall conical shape. Therefore, the distal end portion 18 of the proboscis 12 similarly has a truncated conical shape. More specifically, the proboscis 12 has a circumferential side wall 22, a mid-point portion 24 of which has a constant diameter, which leads to a tapered or conical portion 26 of decreasing diameter in proximity to the distal end portion 18 thereof on which the disposable tip is removably fitted.

The main body 14 of the improved proboscis 12 has a lumen 28 extending axially and centrally therethrough between the proximal end portion 16 and the distal end portion 18. The lumen 28 is in fluid communication with the proximal end bore 20 and the tube which is connected to the metering pump.

The main body 14 of the proboscis 12 further includes at least one orifice 30 through which air is aspirated or expelled in order to selectively draw into the disposable tip or dispense therefrom a specific volume of a sample liquid, such as blood, serum, a chemical reagent or the like. The at least one orifice 30 is formed in the distal end portion 18 of the proboscis 12 and is in fluid communication with the lumen 28 extending axially through the main body 14 thereof.

In a more preferred form of the present invention, the side wall 22 of the main body 14 of the proboscis 12 includes a radially recessed portion 32 situated at the distal end portion 18 of the main body. This recessed portion 32 extends circumferentially about the side wall 22 and, therefore, has a smaller outer diameter than the outer diameter of the side wall 22 directly preceding the recessed portion 32. Even more preferably, the orifice 30 is formed as four radially disposed bores 34 extending through the thickness of the side wall 22 and situated at the recessed portion 32 of the side wall. Each radially disposed bore 34 is in fluid communication with and interconnects at preferably a right angle to the axially disposed lumen 28 foamed through the main body 14. Thus, adjacent bores 34 are separated from each other circumferentially about the recessed portion 32 of the side wall 22 by preferably 90 degrees. Of course, it is envisioned to be within the scope of the present invention to have a fewer or greater number of bores 34 formed at the distal end portion 18 of the main body 14. When the improved proboscis 12 is coupled to the metering pump, a partial vacuum or partial pressure within the proboscis lumen 28 and interconnected radially disposed bores 34, and concomitantly, the disposable tip fitted on the distal end portion 18 of the proboscis, may be created in order to selectively draw into the tip or dispense therefrom a specific volume of a sample liquid.

The sample liquid contained in the disposable tip sometimes may splash when the proboscis is moved, and as a result may come in contact with the orifice 10 on conventional proboscises 2. Because of its sticky nature, the sample liquid may coagulate on, coat or clog the proboscis orifice 10. As will be described in greater detail, the improved proboscis 12 of the present invention includes structure which minimizes the chance that such sample liquid contacts the proboscis orifice 30, or if it does, the orifice 30 and lumen 28 are less likely to become constricted or clogged.

Figure 7:
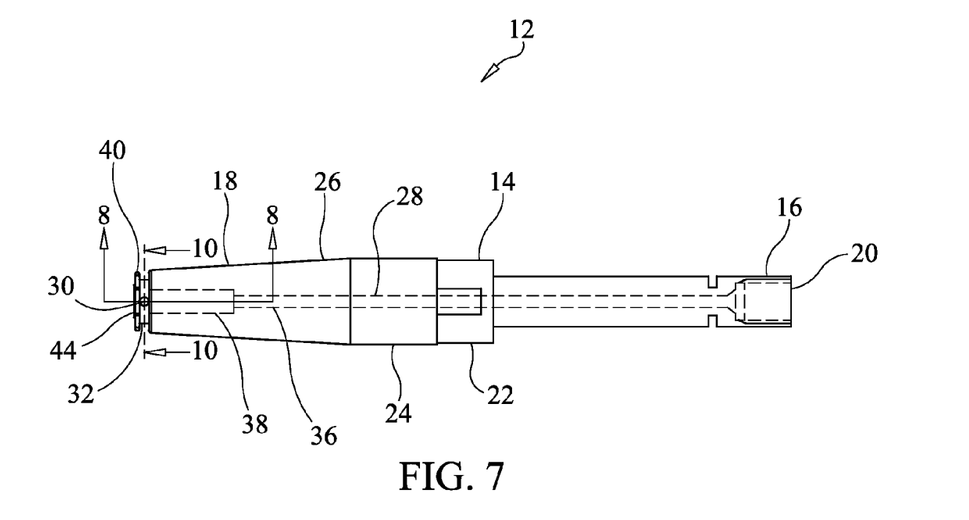
FIG. 7 is a side elevational view in partial cross-section of the improved proboscis of the present invention.

The lumen 28 of the improved proboscis 12 of the present invention preferably includes an enlarged diameter over at least a portion thereof nearer to where the orifice bores 34 are situated. More specifically, and as shown in FIG. 7 of the drawings, the lumen 28 is formed with a first segment 36 and a second segment 38 disposed axially adjacent the first segment 36 and in fluid communication therewith. The first segment 36 is situated in proximity to the first end portion (the proximal end portion) 16 of the main body 14, and the second segment 38 is situated in proximity to the second end portion (the distal end portion) 18 of the main body 14. The orifice 30, and in particular, the four radially disposed bores 34 preferably defining the orifice 30, are in fluid communication with the second segment 38 of the lumen 28. The second segment 38 of the lumen 28 has a diameter which is greater than the diameter of the first segment 36 of the lumen. The enlarged diameter second segment 38 of the lumen 28, being situated at the distal end portion 18 of the proboscis 12, is less likely to become clogged or constricted by any sample fluid coming in contact with the orifice 30 or lumen 28 of the proboscis 12.

The improved proboscis 12 of the present invention further includes a fluid splash guard 40. The splash guard 40 is affixed to the main body 14 of the proboscis 12 at the second end portion (the distal end portion) 18 thereof. The splash guard 40 is situated in proximity to the at least one orifice 30, and is more distally located on the main body 14 than the at least one orifice 30 is located.

More specifically, and as shown in the drawings, the splash guard 40 is preferably generally in the form of a disk which is situated at the tip of the distal end portion 18 of the main body 14 of the proboscis 12, in front of the recessed portion 32 of the proboscis side wall 22 and in front of the four radially disposed orifice bores 34 situated in the recessed portion 32. The splash guard 40 is preferably a solid disk, although it may be formed with a central opening 42 in alignment with the larger diameter, second segment 38 of the lumen 28 so that the second segment 38 may be formed by boring or drilling axially through the opening 42 in the splash guard 40. Then, the opening 42 in the splash guard 40 is closed by sealing it with a plug 44, such as by welding the plug 44 to the splash guard 40.

Preferably, the splash guard 40 is made of the same material as the main body 14 of the proboscis 12, such as stainless steel, and may be formed simultaneously with the main body 14 and be an integral component thereof.

Figure 9:
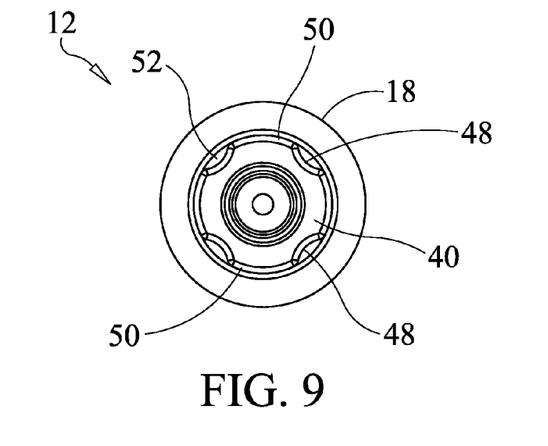
FIG. 9 is an elevational view of the distal end of the improved proboscis of the present invention.
Figure 10:
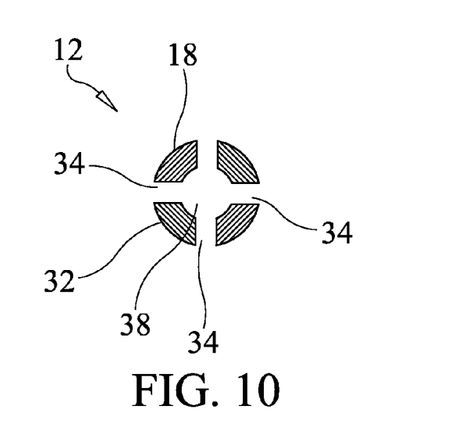
FIG. 10 is a cross-sectional view of the improved proboscis of the present invention shown in FIG. 7, taken along line 10-10 of FIG. 7.
Figure 11:
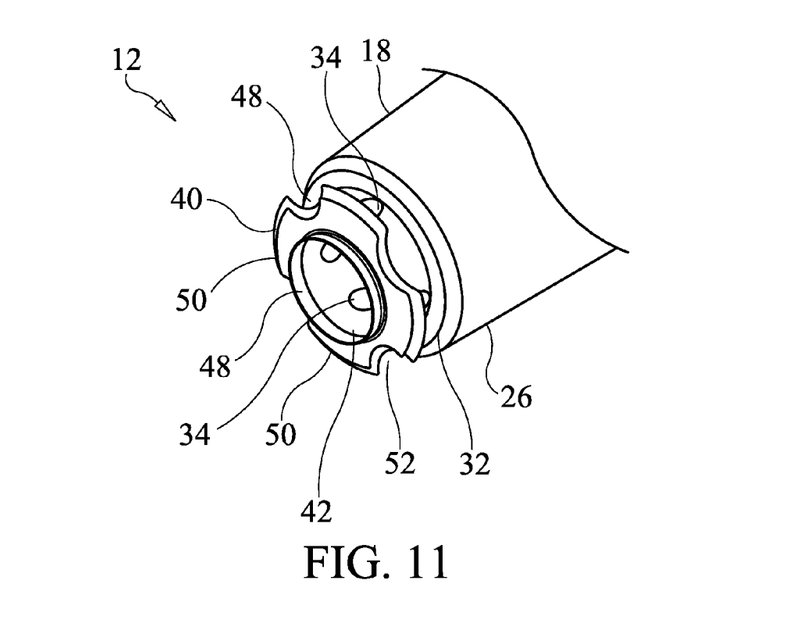
FIG. 11 is a front perspective view of a portion of the improved proboscis of the present invention.
Figure 12:
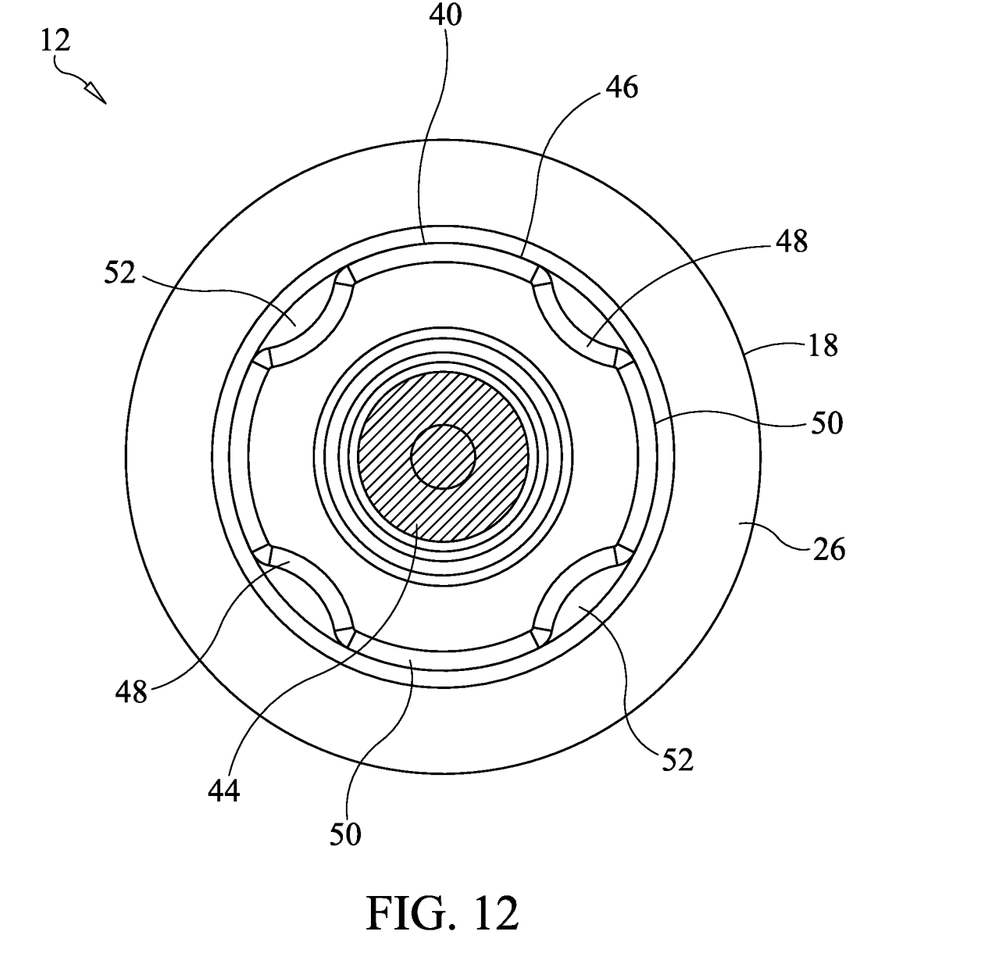
FIG. 12 is a detailed elevational view of the distal end of the improved proboscis of the present invention shown in FIG. 9.

As can be seen from FIGS. 9, 11 and 12 of the drawings, the splash guard 40 includes a radially extending outer peripheral edge 46, with at least portions of the outer peripheral edge 46 extending radially outwardly more than the recessed portion 32 of the side wall 22 in which the radially disposed orifice bores 34 are formed. Even more preferably, the peripheral edge 46 of the splash guard 40 is undulated in structure to define recessed portions 48 of the peripheral edge 46 and non-recessed portions 50 of the peripheral edge interspersed with the recessed portions 48 of the peripheral edge in an alternating fashion.

As can be seen from FIG. 11 of the drawings, each non-recessed portion 50 of the peripheral edge 46 of the splash guard 40 is in longitudinal axial alignment with a respective radially disposed orifice bore 34 which resides in the recessed portion 32 of the side wall 22. Thus, the non-recessed portions 50 are disposed in front of corresponding radially disposed orifice bores 34, and act to block any sample liquid or reagent within the disposable tip that is splashed upwardly towards the distal end portion 18 of the proboscis 12 from entering into or contacting the orifice bores 34 directly behind the non-recessed portions 50 of the splash guard 40.

Figure 8:
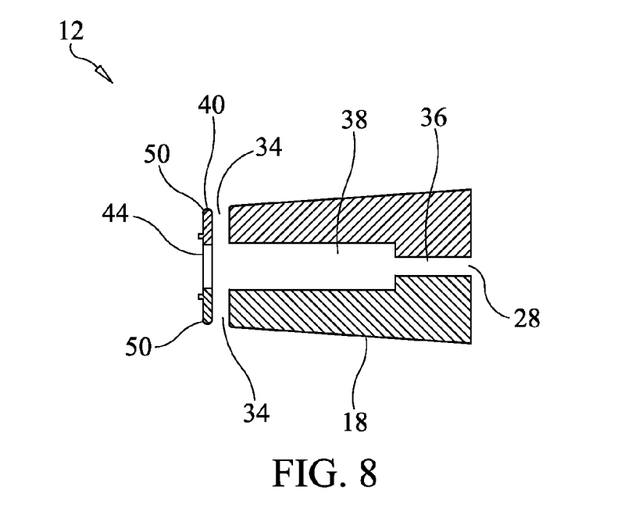
FIG. 8 is a cross-sectional view of a portion of the improved proboscis on the present invention shown in FIG. 7, taken along line 8-8 of FIG. 7.

As one can see from FIGS. 7, 8 and 11 of the drawings, the overall diameter of the splash guard 40, measured between opposite non-recessed portions 50 of the peripheral edge 46 thereof; is preferably equal to or slightly less than the axially receding diameter of the conically shaped portion 26 of the side wall 22, measured at a point where the splash guard 40 resides. This allows the non-recessed portions 50 of the peripheral edge 46 of the splash guard 40 to contact or be in close proximity to the inner surface of the conically shaped disposable tip which is mounted on the distal end portion 18 of the proboscis 12. Accordingly, the recessed portions 48 of the peripheral edge 46 of the splash guard 40 define with the inner surface of a disposable tip mounted on the proboscis 12 channels 52 for air to flow through, that is, from the inside of the disposable tip, through the recessed edge portions 48 of the splash guard 40, and through the orifice bores 34 that lead to and communicate with the axial lumen 28 within the main body 14 of the proboscis 12.

The recessed portions 48 of the peripheral edge 46 of the splash guard 40 are preferably offset circumferentially from the radially disposed bores 34 by a particular angle (45 degrees, if the proboscis 12 is formed with four orifice bores 34, and four non-recessed edge portions 50 and four recessed edge portions 48 of the splash guard 40) so that the air flows along a tortuous path from the interior of the disposable tip mounted on the proboscis 12, through the channels 52 defined by the recessed edge portions 48 of the splash guard 40, into the recessed portion 32 of the proboscis side wall 22, into the radially disposed orifice bores 34 and then through the axially disposed lumen 28 of the main body 14. This tortuous air flow path helps to further isolate the lumen 28 and orifice bores 34 from any splashed liquid or liquid particles entrained in the air.

The improved proboscis 12 of the present invention, with its splash guard 40 and its enlarged lumen 28, is less likely to have its lumen 28 or orifice 30 coated or clogged by sample liquids or reagents contained in the disposable tip mounted thereon. It is anticipated that the accuracy of sample metering, when using the proboscis 12 of the present invention, will be less affected over time than if a conventional proboscis 2, such as shown in FIGS. 1-3 and described previously, is used.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A proboscis for use with a diagnostic instrument, which comprises:

an elongated main body, the main body having a first end portion and a second end portion disposed axially opposite the first end portion, the main body having a lumen extending axially therethrough between the first end portion and the second end portion, the second end portion having at least one orifice formed therein which is in fluid communication with the lumen; and fluid splash guard means for guarding the at least one orifice from contact with fluid in proximity to the second end portion of the elongated main body, the splash guard means being affixed to the main body at the second end portion thereof, the splash guard means being situated in proximity to the at least one orifice and being more distally located than the at least one orifice on the main body;

wherein the main body includes a side wall;

wherein the at least one orifice is disposed on the side wall;

wherein the at least one orifice is in the form of a bore which extends radially through the side wall of the main body the at least one radially disposed bore being in fluid communication with the axially disposed lumen;

wherein the side wall of the main body includes a radially recessed portion situated at the second end portion;

and wherein the at least one radially disposed bore is situated at the radially recessed portion of the side wall.

2. A proboscis as defined by claim 1, wherein the elongated main body has a longitudinal axis along which the elongated main body extends;

and wherein the fluid splash guard means is in the form of a solid, non-apertured member which extends outwardly from the elongated main body in a radial direction with respect to the longitudinal axis of the main body.

3. A proboscis as defined by claim 1, wherein the fluid splash guard means is in the form of a solid, non-apertured, generally disk-shaped member.

4. A proboscis for use with a diagnostic instrument, which comprises:

an elongated main body, the main body having a first end portion and a second end portion disposed axially opposite the first end portion, the main body having a lumen extending axially therethrough between the first end portion and the second end portion, the second end portion having at least one orifice formed therein which is in fluid communication with the lumen; and a fluid splash guard, the splash guard being affixed to the main body at the second end portion thereof, the splash guard being situated in proximity to the at least one orifice and being more distally located than the at least one orifice on the main body;

wherein the main body includes a side wall;

wherein the at least one orifice is disposed on the side wall;

wherein the at least one orifice is in the form of a bore which extends radially through the side wall of the main body, the at least one radially disposed bore being in fluid communication with the axially disposed lumen;

wherein the side wall of the main body includes a radially recessed portion situated at the second end portion;

wherein the at least one radially disposed bore is situated at the radially recessed portion of the side wall;

and wherein the splash guard is generally in the form of a disk and includes a radially extending outer peripheral edge, at least portions of the outer peripheral edge extending radially outwardly more than the recessed portion of the side wall in which the at least one radially disposed bore is formed.

5. A proboscis as defined by claim 4, wherein the at least one radially disposed bore includes a plurality of radially disposed bores formed through the recessed portion of the side wall and circumferentially spaced apart from one another;

and wherein the peripheral edge of the splash guard is undulated to define recessed portions of the peripheral edge and non-recessed portions of the peripheral edge interspersed with the recessed portions of the peripheral edge, each non-recessed portion of the peripheral edge of the splash guard being in longitudinal axial alignment with a respective radially disposed bore of the plurality of radially disposed bores formed in the recessed portion of the side wall.

6. A proboscis for use with a diagnostic instrument, which comprises:

an elongated main body, the main body having a first end portion and a second end portion disposed axially opposite the first end portion, the main body having a lumen extending axially therethrough between the first end portion and the second end portion, the second end portion having at least one orifice formed therein which is in fluid communication with the lumen; and a fluid splash guard, the splash guard being affixed to the main body at the second end portion thereof, the splash guard being situated in proximity to the at least one orifice and being more distally located than the at least one orifice on the main body;

wherein the lumen includes a first lumen segment and a second lumen segment disposed axially adjacent the first lumen segment and in fluid communication therewith, the first lumen segment being situated in proximity to the first end portion of the main body, the second lumen segment being situated in proximity to the second end portion of the main body, the at least one orifice being in fluid communication with the second lumen segment;

and wherein the second lumen segment has a diameter which is greater than the diameter of the first lumen segment.

7. A proboscis for use with a diagnostic instrument, which comprises:

an elongated main body, the main body having a first end portion and a second end portion disposed axially opposite the first end portion, the main body having a lumen extending axially therethrough between the first end portion and the second end portion, the second end portion having a plurality of orifices formed therein which are in fluid communication with the lumen, the plurality of orifices being spaced apart from each about the circumference of the main body of the proboscis to provide a tortuous air flow path therethrough and into or out of the lumen; and fluid splash guard means for guarding the plurality of orifices from contact with fluid in proximity to the second end portion of the elongated main body, the splash guard means being situated in proximity to the plurality of orifices and being more distally located than the plurality of orifices on the main body.

8. A proboscis as defined by claim 7, wherein the main body includes a side wall, and wherein each orifice of the plurality of orifices is formed as a bore which extends radially through the side wall of the main body and interconnects with the lumen at substantially a right angle to a longitudinal axis of the lumen to thereby at least partially provide a tortuous air flow path therethrough and into or out of the lumen.

9. A proboscis as defined by claim 7, wherein the fluid splash guard means is in the form of a solid, non-apertured, generally disk-shaped member.

10. A proboscis for use with a diagnostic instrument, which comprises:

an elongated main body, the main body having a first end portion, a second end portion disposed axially opposite the first end portion and a side wall, the main body having a lumen extending axially therethrough between the first end portion and the second end portion, the second end portion having at least one orifice formed therein which is in fluid communication with the lumen, the at least one orifice being formed as a bore which extends radially through the side wall of the main body and interconnects with the lumen at substantially a right angle thereto; and a fluid splash guard, the splash guard being affixed to the main body at a second end portion thereof, the splash guard being situated in proximity to the at least one orifice and being more distally located than the at least one orifice on the main body, the fluid splash guard having a peripheral edge in which at least a recessed edge portion is formed to at least partially define an air flow channel, the air flow channel of the fluid splash guard being in fluid communication with the at least one orifice and the lumen, the air flow channel, the at least one orifice and the lumen together defining a tortuous path for air to flow into or out of and through the proboscis.

11. A proboscis for use with a diagnostic instrument, which comprises:

an elongated main body, the main body having a first end portion and a second end portion disposed axially opposite the first end portion, the main body having a lumen extending axially therethrough between the first end portion and the second end portion, the second end portion having a plurality of orifices formed therein which are in fluid communication with the lumen, the plurality of orifices providing an increased area of air flow therethrough and into or out of the lumen; and fluid splash guard means for guarding the plurality of orifices from contact with fluid in proximity to the second end portion of the elongated main body, the splash guard means being situated in proximity to the plurality of orifices and being more distally located than the plurality of orifices on the main body.

12. A proboscis as defined by claim 11, wherein the main body includes a side wall, and wherein each orifice of the plurality of orifices is formed as a bore which extends radially through the side wall of the main body, the orifices interconnecting with the lumen at spaced apart points on the lumen, thereby providing an increased area and tortuous path for air to flow into or out of the proboscis.

13. A proboscis as defined by claim 11, wherein the fluid splash guard means is in the form of a solid, non-apertured, generally disk-shaped member.

14. A proboscis for use with a diagnostic instrument, which comprises:

an elongated main body, the main body having a first end portion and a second end portion disposed axially opposite the first end portion, the main body having a lumen extending axially therethrough between the first end portion and the second end portion, the second end portion having a plurality of orifices formed therein which are in fluid communication with the lumen, the plurality of orifices providing an increased area of air flow therethrough and into or out of the lumen;

wherein the main body includes a side wall, and wherein each orifice of the plurality of orifices is formed as a bore which extends radially through the side wall of the main body, the orifices interconnecting with the lumen at spaced apart points on the lumen, thereby providing an increased area and tortuous path for air to flow into or out of the proboscis; and wherein the lumen includes a first lumen segment and a second lumen segment disposed axially adjacent the first lumen segment and in fluid communication therewith, the first lumen segment being situated in proximity to the first end portion of the main body, the second lumen segment being situated in proximity to the second end portion of the main body, the plurality of orifices being in fluid communication with the second lumen segment;

and wherein the second lumen segment has a diameter which is greater than the diameter of the first lumen segment.

15. A proboscis for use with a diagnostic instrument, which comprises:

an elongated main body, the main body having a first end portion and a second end portion disposed axially opposite the first end portion, the main body having a lumen extending axially therethrough between the first end portion and the second end portion, the second end portion having a plurality of orifices formed therein which are in fluid communication with the lumen; and means defining a plurality of tortuous paths for air to flow into or out of the main body of the proboscis, the tortuous air flow path defining means being situated on the main body at the second end portion thereof;

wherein the tortuous air flow path defining means includes a generally disk-shaped component having a radially extending outer peripheral edge, the peripheral edge of the disk-shaped component being undulated to define recessed portions of the peripheral edge and non-recessed portions of the peripheral edge interspersed with the recessed portions of the peripheral edge, each non-recessed portion of the peripheral edge of the disk-shaped component being in longitudinal axial alignment with a respective orifice of the plurality of orifices, the recessed portions of the peripheral edge of the disk-shaped component at least partially define air flow channels, the air flow channels of the disk-shaped component being in fluid communication with the orifices and the lumen, the air flow channels at least partially defined by the recessed portions of the peripheral edge of the disk-shaped component being out of longitudinal axial alignment with the orifices, thereby defining tortuous paths for air to flow through the air flow channels and into or out of the orifices in fluid communication with the lumen.

16. In combination:

a proboscis for use with a diagnostic instrument, and a disposable tip removably mountable on the proboscis, the disposable tip having a side wall, the side wall having an inner surface, the proboscis comprising:

an elongated main body, the main body having a first end portion and a second end portion disposed axially opposite the first end portion, the main body having a lumen extending axially therethrough between the first end portion and the second end portion, the second end portion having a plurality of orifices fanned therein which are in fluid communication with the lumen; and a fluid splash guard, the splash guard being situated on the main body at the second end portion thereof, the splash guard being generally in the form of a disk and including a radially extending outer peripheral edge, the peripheral edge of the splash guard being undulated to define recessed portions of the peripheral edge and non-recessed portions of the peripheral edge interspersed with the recessed portions of the peripheral edge, each non-recessed portion of the peripheral edge of the splash guard being in longitudinal axial alignment with a respective orifice of the plurality of orifices, the recessed portions of the peripheral edge of the splash guard defining with the inner surface of the side wall of the disposable tip air flow channels when the disposable tip is mounted on the proboscis, the air flow channels being in fluid communication with the orifices and the lumen, the air flow channels defined by the recessed portions of the peripheral edge of the splash guard and the inner surface of the side wall of the disposable tip being out of longitudinal axial alignment with the orifices, thereby defining tortuous paths for air to flow through the air flow channels and into or out of the orifices in fluid communication with the lumen.

* * * * *